United States Patent
Goldberg et al.

(10) Patent No.: US 10,632,277 B2
(45) Date of Patent: Apr. 28, 2020

(54) VIRTUAL REALITY GUIDED MEDITATION IN A WELLNESS PLATFORM

(71) Applicant: Odyssey Science Innovations, LLC, Lake Oswego, OR (US)

(72) Inventors: Alex Jeffrey Goldberg, Lake Oswego, OR (US); Aaron Serling Goldberg, Portland, OR (US)

(73) Assignee: THE STAYWELL COMPANY, LLC, Yardley, PA (US)

( * ) Notice: Subject to any disclaimer, the term of this patent is extended or adjusted under 35 U.S.C. 154(b) by 456 days.

(21) Appl. No.: 15/134,333

(22) Filed: Apr. 20, 2016

(65) Prior Publication Data
US 2017/0304585 A1    Oct. 26, 2017

(51) Int. Cl.
*A61M 21/02*    (2006.01)
*G16H 15/00*    (2018.01)
*A61M 21/00*    (2006.01)

(52) U.S. Cl.
CPC ............ *A61M 21/02* (2013.01); *G16H 15/00* (2018.01); *A61M 2021/005* (2013.01); *A61M 2021/0027* (2013.01); *A61M 2205/502* (2013.01)

(58) Field of Classification Search
CPC .... A61B 5/0482; A61B 5/6801; A61M 21/02; A61M 2021/0027; A61M 2021/005; A61M 2205/502; G16H 15/00
See application file for complete search history.

(56) References Cited

U.S. PATENT DOCUMENTS

| 2002/0128540 A1* | 9/2002 | Kim | A61B 5/486 600/301 |
| 2009/0269329 A1* | 10/2009 | Hyde | G06F 19/3481 424/130.1 |
| 2011/0230732 A1* | 9/2011 | Edman | A61B 5/4869 600/301 |

(Continued)

OTHER PUBLICATIONS

"Virtual Reality Relaxation / Meditation for Oculus Rift DK2: Guided Meditation VR," Cubicle Ninjas, undated, 3 pages, [Online] [Retrieved on May 13, 2016] Retrieved from the Internet<URL:http://guidedmeditationvr.com/>.

(Continued)

*Primary Examiner* — Xuan M Thai
*Assistant Examiner* — Malina D. Blaise
(74) *Attorney, Agent, or Firm* — Fenwick & West LLP

(57) ABSTRACT

A method for providing guided meditation to a user in a virtual reality environment is provided. A user selects a type of meditation, time duration of meditation, and location of meditation. Based on the user's selections, the VR guided meditation system provides a guided meditation exercise and a VR environment to a client device. The guided meditation exercise includes audio instructions guiding the user through meditation steps. The VR environment includes imagery corresponding to the selected location for the meditation exercise, for example, imagery of a beach, waterfall, or trees. The VR guided meditation system also generates reports including statistics of data from a population of users completing guided meditation exercises. For instance, the population of users includes employees of an employer. The report is provided to the employer for the employer to track workplace wellness of the employees.

20 Claims, 7 Drawing Sheets

(56) References Cited

U.S. PATENT DOCUMENTS

| | | | | |
|---|---|---|---|---|
| 2013/0089851 A1* | 4/2013 | Drane | ................... | G09B 5/06 |
| | | | | 434/362 |
| 2013/0211238 A1* | 8/2013 | DeCharms | ............ | A61B 5/4824 |
| | | | | 600/418 |
| 2015/0223731 A1* | 8/2015 | Sahin | ................ | A61B 5/16 |
| | | | | 600/301 |
| 2015/0297109 A1* | 10/2015 | Garten | ................ | A61B 5/04845 |
| | | | | 600/544 |
| 2015/0351655 A1* | 12/2015 | Coleman | ............. | A61B 5/0482 |
| | | | | 600/301 |
| 2016/0005320 A1* | 1/2016 | deCharms | .............. | G09B 5/065 |
| | | | | 434/236 |
| 2016/0048027 A1* | 2/2016 | Shpigelman | ............. | G06T 15/00 |
| | | | | 345/156 |
| 2016/0077547 A1* | 3/2016 | Aimone | ................. | G06F 3/012 |
| | | | | 345/8 |
| 2016/0170996 A1* | 6/2016 | Frank | ............... | G06F 16/24578 |
| | | | | 707/748 |
| 2017/0162072 A1* | 6/2017 | Horseman | ............... | A61B 5/002 |
| 2017/0188976 A1* | 7/2017 | Kalra | ..................... | A61B 5/165 |
| 2017/0189815 A1* | 7/2017 | Tweedale | ................ | A63F 13/79 |

OTHER PUBLICATIONS

"Headspace: The Science Behind Meditation," Headspace Inc., 2016, 7 pages, , [Online] [Retrieved on May 13, 2016] Retrieved from the Internet<URL:https://www.headspace.com/science>.

* cited by examiner

VIRTUAL REALITY GUIDED MEDITATION IN A WELLNESS PLATFORM

BACKGROUND

This disclosure relates generally to the field of guided meditation, and specifically to providing guided meditation to a user in a virtual reality environment.

Meditation can provide numerous physical and mental benefits. For example, on a physical level, meditation may increase a person's energy level, lower high blood pressure, improve the immune system, and reduce tension-based pain. On a mental level, meditation may, for example, decrease stress and anxiety, increase happiness, improve emotional stability, and achieve peace of mind. People who practice meditation regularly are more likely to experience these benefits. Guided meditation is a form of meditation in which a person follows voice instructions, either live or recorded, guiding the person step-by-step through a meditation exercise.

Meditating outdoors in nature may facilitate improved meditation experiences compared to meditating indoors. Natural environments such as beaches, oceans, forests, waterfalls, and other pleasant settings can help people relax and focus while meditating. However, it may be impractical for people who do not live or work near these natural environments to meditate in natural environments. Virtual reality technology can let users view these environments through a virtual reality system. For example, the virtual environment may be a natural environment located across the world from the location of a user in real life.

SUMMARY

A method for providing guided meditation to a user in a virtual reality environment is provided. A VR guided meditation system receives information from a client device of a user such as a smart phone running a VR guided meditation application. The information includes a request for a guided meditation exercise and selections for the exercise. For instance, the user may select a type of meditation such as a meditation that focuses on breathing patterns or a meditation that involves a "body scan" of the user. Further, the user selects a time duration of the meditation exercise and a location of the meditation exercise. The location options include natural environments that are suitable for meditation such as a beach, a waterfall, and a forest. Based on the user's selections, the VR guided meditation system provides a guided meditation exercise and a VR environment to the smart phone device. In particular, the guided meditation exercise includes audio instructions guiding the user through the exercise. The audio instructions are played to the user via speakers of the smart phone or headphones connected to the smart phone. The VR environment is presented to the user via the display of the smart phone. The VR environment includes 360 degree imagery corresponding to the selected location for the meditation exercise, for example, imagery of a beach, waterfall, or trees. To help provide an immersive VR environment for the user completing the guided meditation exercise, visual elements and/or events in the VR environment are synchronized with steps of the guided meditation exercise. For example, a step informs the user to look at the waterfall imagery in the VR environment while exhaling a breath slowly.

The VR guided meditation system also generates reports including statistics of data and usage trends from a population of users (e.g., a group of users with similar characteristics, such as a group of employees of a company) completing guided meditation exercises. For instance, the population of users may include employees of an employer or members of an insurance plan covered by an employer. The population of users may also include a group of users in general. The report is provided to the employer for the employer to track the wellness of the employees, covered member populations, and/or users in general. For example, the employer can track usage trends and the average number of minutes that each employee meditates per day. The system may also provide feedback to the user based on the user's personal usage and trends of the user's data relative to trends of a larger population. Further, the users may receive incentives for achieving certain goals through the guided meditation exercises. For instance, an employee who meditates at least 500 minutes in a month receives a coupon for meditation related products or a lower deductible for a health insurance plan. The VR guided meditation system and reports may assist employers in promoting workplace wellness and healthy practices among employees such as regular practice of meditation.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

System Overview

Figure 1:
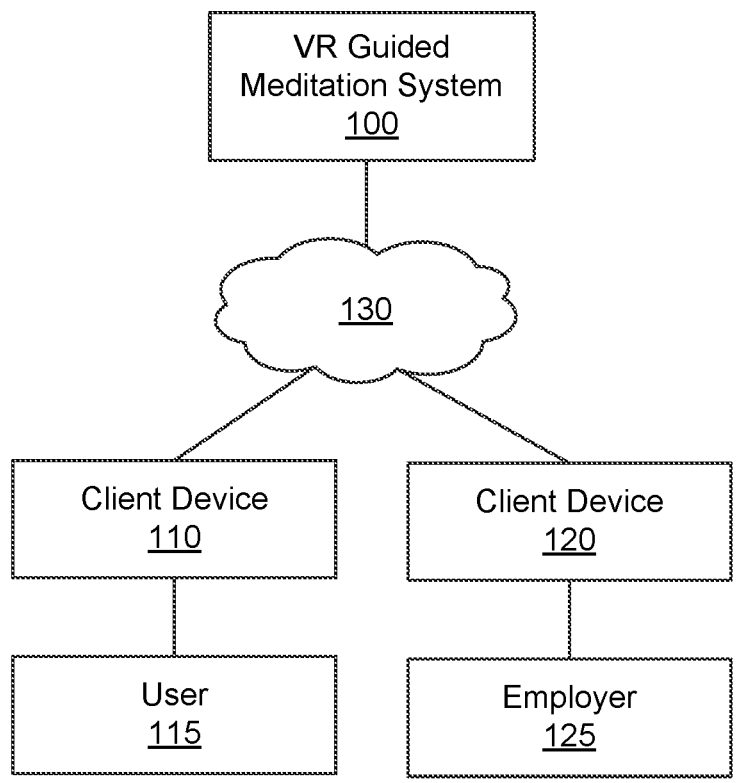
FIG. 1 is a block diagram of a computing environment for guided meditation with a VR guided meditation system according to one embodiment.

FIG. 1 is a block diagram of a computing environment for guided meditation with a VR guided meditation system 100 according to one embodiment. The VR guided meditation system 100 is connected to the network 130 and includes various modules described in FIG. 2. A user 115 interacts with the system 100 via a user interface of the client device 110 connected to the network 130. Further, an employer 125 interacts with the system 100 via a user interface of the client device 120 connected to the network 130. In some embodiments, the employer 125 is another type of individual or entity. For example, the employer 125 is instead an administrator 125 of a health wellness program or an insurance plan. In this case, the users 115 are, e.g., participants of the health wellness program or covered members of the insurance plan, respectively. That is, in some embodiments, the users 115 are users in general and not necessarily employees of the employer 125. Some embodiments of the system 100 may have additional, fewer, and/or different modules than the ones described herein and have more than two client devices (i.e., client device 110 and client device 120), users 115, and employers 125. The functions can be distributed among the modules in a different manner than described in FIG. 1.

A client device, e.g., client device 110 and 120, is an electronic device used by a user, e.g., user 115 and employer 125, to perform functions such as executing software applications, consuming digital content, browsing websites hosted by web servers on the network 130, downloading files, and the like. For example, the client device may be a mobile device, a tablet, a notebook, a desktop computer, or a portable computer. The client device includes interfaces with a display device on which the user may view webpages, videos and other content. In addition, the client device provides a user interface (UI), such as physical and/or on-screen buttons with which the user may interact with the client device to perform functions such as viewing, selecting, and consuming digital content such as digital medical records, webpages, photos, videos and other content.

The network 130 enables communications among network entities such as the client device 110, the client device 120, and the VR guided meditation system 100. In one embodiment, the network 130 comprises the Internet and uses standard communications technologies and/or protocols, e.g., BLUETOOTH®, WiFi, ZIGBEE®, clouding computing, other air to air, wire to air networks, and mesh network protocols to client devices, gateways, and access points. In another embodiment, the network entities can use custom and/or dedicated data communications technologies.

In one embodiment, the VR guided meditation system 100 receives information from the user 115 via the client device 110. For instance, the information includes a request for a guided meditation exercise. Further, the information indicates a type of meditation, time duration for meditation, and location for meditation along with the request. Based on the information, the VR guided meditation system 100 provides a VR guided meditation exercise to the user 115 via the client device 110. Additionally, the VR guided meditation system 100 generates a report based on the VR guided meditation exercise, as well as previously provided VR guided meditation exercises. The VR guided meditation system 100 provides the report to an employer 125 of the user 115 via the client device 120.

Figure 2:
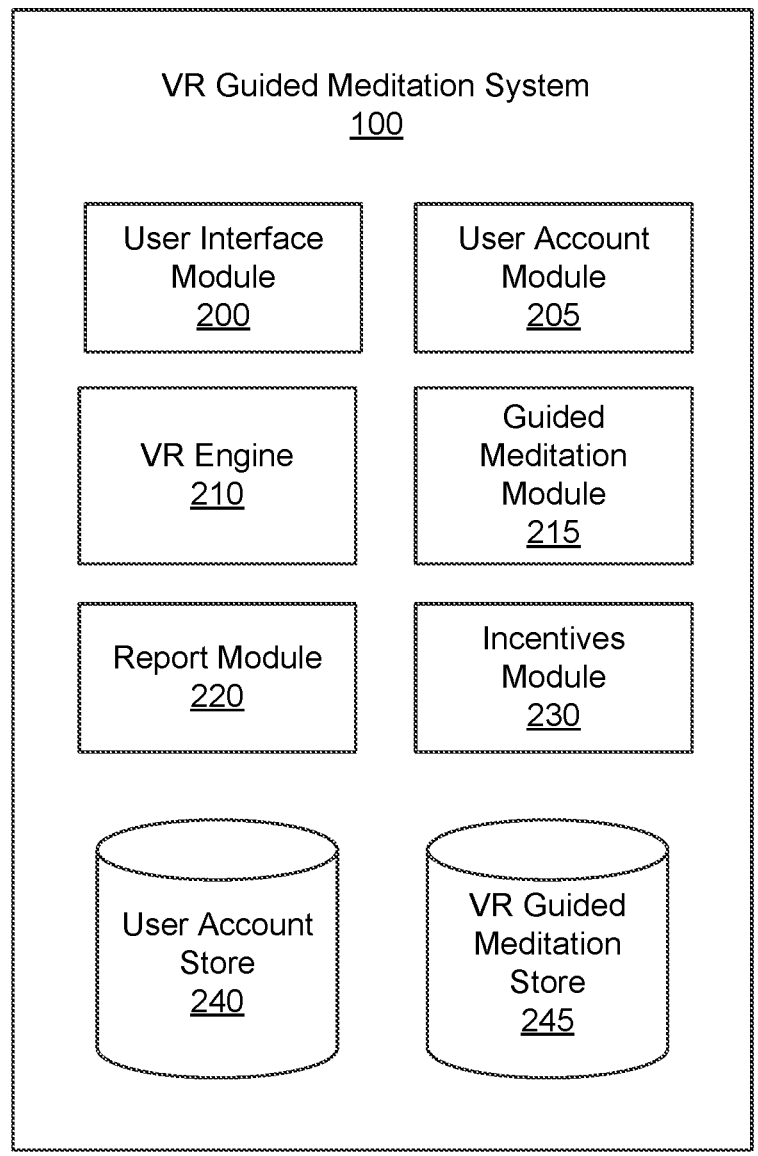
FIG. 2 is a block diagram of the VR guided meditation system within the computing environment of FIG. 1 according to one embodiment.

FIG. 2 is a block diagram of the VR guided meditation system 100 within the computing environment of FIG. 1 according to one embodiment. The VR guided meditation system 100 in FIG. 2 includes a user interface module 200, user account module 205, VR engine 210, guided meditation module 215, report module 220, incentives module 230, user account store 240, and VR guided meditation store 245. In other embodiments, the VR guided meditation system 100 may include additional, fewer, and/or different modules for various applications. Conventional components such as network interfaces, security mechanisms, load balancers, failover servers, management and network operations consoles, and the like are not shown so as to not obscure the details of the system 100. Also, it is noted that the modules may be embodied as hardware, software (which may include firmware), or any combination thereof. For software, it may include program code or code segments. Software is comprised of one or more instructions storable in a computer readable storage medium, e.g., a memory or disk, and executable by a processor.

The user interface module 200 may be configured to link the VR guided meditation system 100 via the network 130 to the client devices 110 and 120. In an embodiment, the user interface module 200 serves web pages, as well as other web-related content, such as Flash, XML, and so forth. The user interface module 200 provides the functionality of receiving and routing messages and/or information, e.g., between the VR guided meditation system 100 and the client devices 110 and 120, as well as other external systems. These messages can be instant messages, queued messages (e.g., email), text and SMS (short message service) messages, or any other suitable messaging technique. The user interface module 200 allows the user 115 and employer 125 to view and/or interact with user interfaces generated by the system 100 by communicating information between the system 100 and the client devices 110 and 120.

The user account module 205 may be configured to store user account data associated with users 115 of the VR guided meditation system 100. In an embodiment, the user account data of a user 115 includes information including a name of the user, contact information (e.g., email and phone number) of the user, an employer of the user (e.g., employer 125), information about VR guided meditation exercises that the user has previously started and/or completed, incentives that the user has earned, information about a third-party smart device and/software of the user (e.g., FITBIT® and APPLE® HEALTHKIT), and the like. The VR guided meditation system 100 receives the information from the user 115 via the client device 110.

The VR engine 210 may be configured to generate a VR environment associated with a VR guided meditation exercise generated by the guided meditation module 215. In an embodiment, the VR engine 210 extracts VR environment data from the VR guided meditation store 245. The VR environment data may be previously input, e.g., via a client device, to the VR guided meditation store 245 by an expert, e.g., a designer of VR environments. Based on the data, the VR engine 210 generates the VR environment. In an embodiment, the VR environment includes one or more visual and/or audio signals corresponding to a location of the VR environment. For instance, a location of the VR environment is "garden falls" (e.g., the garden falls location shown in FIG. 5). Accordingly, the one or more visual and/or audio signals corresponding to the "garden falls" location includes visual and/or audio signals of waterfalls and garden plants. In particular, a visual signal is a video imagery of a waterfall surrounding by trees and plants with flowers. Further, an audio signal is a sound of water flowing or splashing in the waterfall. The VR engine 210 provides the VR environment to the client device 110, via the user interface module 200, for presentation to the user 115. In particular, the visual signals (e.g., videos and photos) are presented in a graphical display of the client device 110, e.g., a screen display of a smartphone. Additionally, the audio signals are presented via audio speakers of the client device 110 and/or another audio playing device (e.g., headphones or external speakers) communicatively coupled to the client device 110.

The guided meditation module 215 may be configured to generate a VR guided meditation exercise associated with a VR environment generated by the VR engine. In an embodiment, the VR engine 210 extracts meditation exercise data from the VR guided meditation store 245. The meditation exercise data may be previously input, e.g., via a client device, to the VR guided meditation store 245 by an expert, e.g., a meditation instructor or researcher. Based on the data, the VR engine 210 generates the VR guided meditation exercise. In an embodiment, the VR guided meditation exercise includes meditation instructions corresponding to a type of meditation. For instance, a type of meditation is "breathing" (e.g., the breathing type shown in FIG. 3). Accordingly, the meditation instructions related to breathing of a user 115. For example, the instructions include "keep your breath natural" and "notice where you feel your breath in your body."

Figure 4:
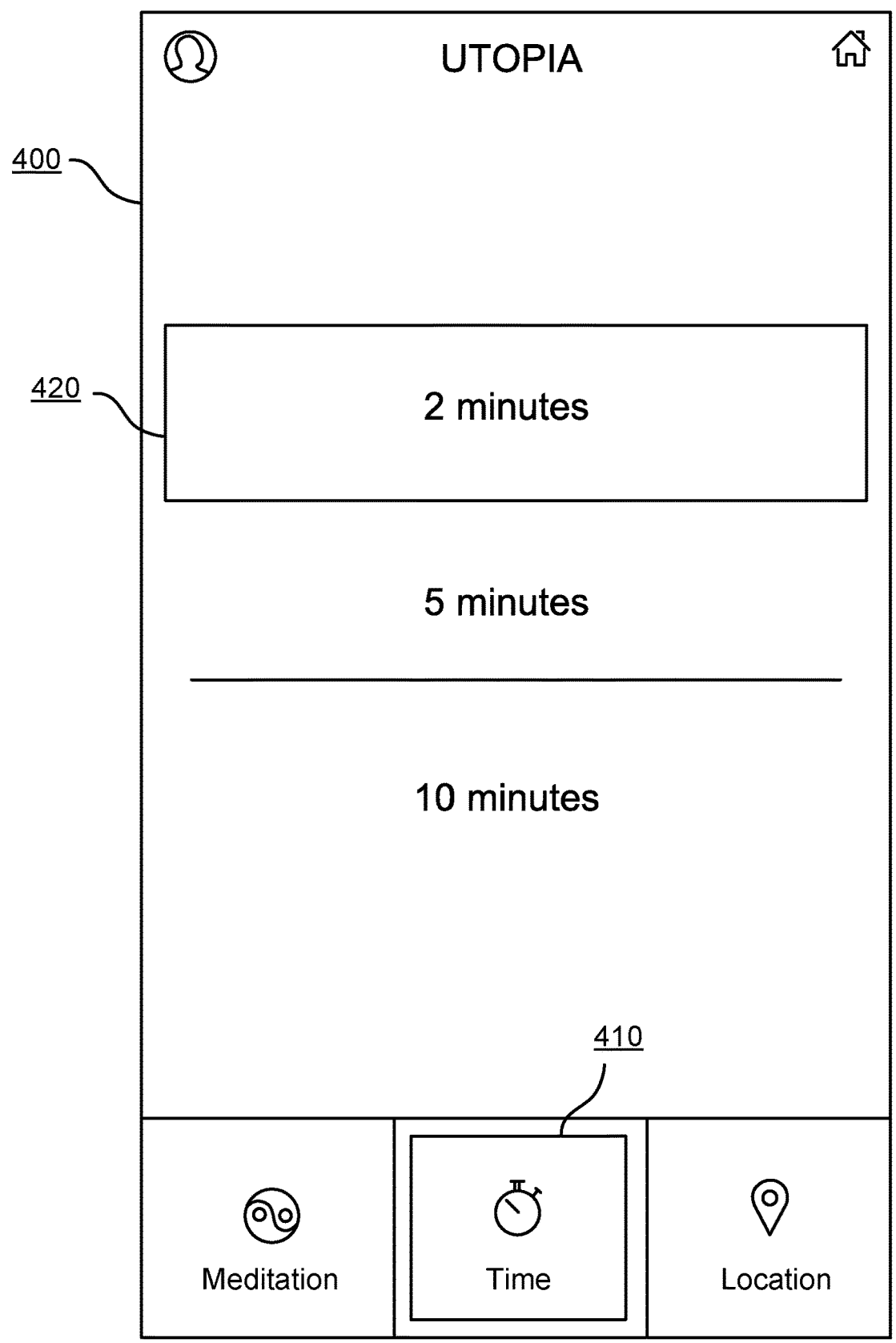
FIG. 4 is user interface illustrating meditation time durations of the VR guided meditation system according to one embodiment.

In an embodiment, the VR guided meditation exercise has a time duration, e.g., a time duration shown in FIG. 4. For a VR guided meditation exercise with a shorter time duration, e.g., 2 minutes, the guided meditation module 215 may reduce the number of meditation instructions such that the VR guided meditation exercise can be completed within the shorter time duration. For a VR guided meditation exercise with a longer time duration, e.g., 10 minutes, the guided meditation module 215 may increase the number or duration of pauses in between meditation instructions such that the VR guided meditation exercise can be completed within the longer time duration. The VR engine 210 provides the meditation instructions to the client device 110, via the user interface module 200, for presentation to the user 115. In particular, the meditation instructions represented by visual signals (e.g., graphical text of the meditation instructions) are presented in a graphical display of the client device 110, e.g., a screen display of a smartphone. Additionally, the meditation instructions represented by audio signals (e.g., an audio narration of the meditation instructions) are presented via audio speakers of the client device 110 and/or another audio playing device (e.g., headphones or external speakers) communicatively coupled to the client device 110.

The report module 220 may be configured to generate a report including statistics of users 115 and VR guided meditation exercises completed by users 115. The report may be presented on a user interface (e.g., user interface 600 further described in FIG. 6) of a client device 120 for an employer 125 to view. The report may also be presented on a user interface of a client device 110 for a user 115 to view. In one example, the statistics indicate the average time users 115, e.g., employees of the employer 125, meditate (i.e., using the VR guided meditation system 100) per office location of the employer 125 per day. In another example, the statistics indicate the average time all employees of the employer 125 meditate per day. In yet another example, the statistics indicate the percentage of all employees of the employer 125 that use the VR guided meditation system 100. Based on the reviewing the statistics, the employer 125 may assess workplace wellness of the employees, make recommendations to employees to improve workplace wellness based on the assessment (e.g., meditating more to help reduce stress among employees, and thus increase employee productivity), compare meditation statistics and/or feedback between different populations of employees (e.g., whether employees at one office location are meditating fewer minutes on average relative to employees at other office locations), set goals for incentives, and the like. In some embodiments, the VR guided meditation system 100 is integrated with a workplace wellness platform associated with an employer 125 and users 115 who are employees of the employer 125. The workplace wellness platform may be a third-party application, e.g., an online website or application running on client devices of users 115 and employers 125. Further, the workplace wellness platform may be integrated with other services such as FITBIT®, APPLE® HEALTH-KIT, health insurance plan services, and the like.

The report module 220 may further be configured to collect data over a period of time about guided meditation exercises performed by users 115. The data may be organized individually by each user or aggregated for a population of users. Based on the collected data and corresponding statistics of the data, the report module 220 can generate reports about individual users and/or the population of users.

The report module 220 may additionally be configured to provide questions to the client device 110 of a user 115. In an embodiment, the questions are presented to the user 115 before the user starts a guided meditation exercise as well as after the user starts a guided meditation exercise. The questions may inform the user 115 to provide, e.g., information describing a current level of stress of the user 115, a location of the user 115 in real life (e.g., office cubicle or balcony), a heart rate of the user 115 (e.g., measured by a third-party device such as a FITBIT®), a current mood of the user 115 (e.g., happy or sad), a recent meal consumed by the user 115 (e.g., whether the user ate fruit for breakfast), and the like. The report module 220 can receive the users' responses to the questions, e.g., via the user interface module 200. In some embodiments, the responses include pre-determined selections for responses. For example, the responses may include Likert-type scale responses such as "strongly disagree," "agree," "neutral," "disagree," and "strongly disagree." In an embodiment, the report module 220 stores the responses in the user account store 240 along with a user account associated with the user 115. Further, in some embodiments, the report module 220 generates reports based on the responses of the user 115. For instance, the report module 220 compares a level of stress of the user 115 before and after completing the guided meditation exercise. The report module 220 generates a report indicating that the user's level of stress was lower after completing the guided meditation exercise, relative to before starting the guided meditation exercise. Thus, the report indicates that the guided meditation exercise may have helped improve the user's level of stress.

The incentives module 230 may be configured to provide incentives to users 115 who perform VR guided meditation exercises. The incentives may be associated with a particular goal, e.g., the incentives module 230 provides an incentive to a user 115 if the user 115 achieves the particular goal. A goal can be achieved by completing a VR guided meditation exercise and/or performing a portion of a VR guided meditation exercise. For instance, a goal is achieved when a user performs at least 100 total minutes of VR guided meditation exercises. A user can achieve this goal during the middle of a VR guided meditation exercise before completing the VR guided meditation exercise. In an embodiment, the incentives to users 115 who are employees of an employer 125 are based on incentive information provided by the employer 125. For instance, the employer 125 provides incentive information to the incentives module 230 indicating that users 115 who complete at least a threshold number of minutes of VR guided meditation exercises earn a certain incentive, e.g., a coupon for a discount on health and wellness related products such as exercise apparel and water bottles. The incentives module 230 provides the coupon incentive, e.g., as a digital coupon via a client device 110, to a user 115 who earns the coupon incentive. The threshold number of minutes may be a cumulative number of minutes or an average number of minutes over a time period, e.g., a latest month. Further, the threshold number of minutes can be manually selected by the employer 125 or automatically set by the incentives module 230. For instance, the incentives module 230 automatically sets the threshold number of minutes based on data of a population of users 115, e.g., the threshold number of minutes is equivalent to the number of minutes that the top 10% of users 115 meditate on average each month. In an embodiment, populations of users 115 is determined based on users 115 who are employees at a particular office location of an employer 125. Incentives based on these populations may promote competition between employees of different office locations (or within one office location), and thus result in increased use of the VR guided meditation system 100 among employees.

In some embodiments, incentives module 230 categorizes incentives into different tiers of incentives. For example, users 115 earn tier 1 awards by satisfying a first set of one or more criteria, e.g., complete ten VR guided meditation exercises in the latest month; users 115 earn tier 2 awards by satisfying a second set of one or more criteria, e.g., complete twenty VR guided meditation exercises in the latest month; users 115 earn tier 3 awards by satisfying a third set of one or more criteria, e.g., complete a VR guided meditation exercises every day in the latest month.

In some embodiments, incentives module 230 provides virtual incentives, for completing VR guided meditation exercises, associated with a user account of a user 115. For example, a virtual incentive is a badge indicating an achievement of a user 115 (e.g., completed 100 total VR guided meditation exercises). The virtual incentive is viewable user interfaces of client devices 110 of the user 115 and other users. Thus, as a result of earning the virtual incentive, the user 115 may receive recognition from other users such as other employees, i.e., co-workers of the user 115, as well as an employer 125 of the user 115.

User Interfaces

Figure 3:
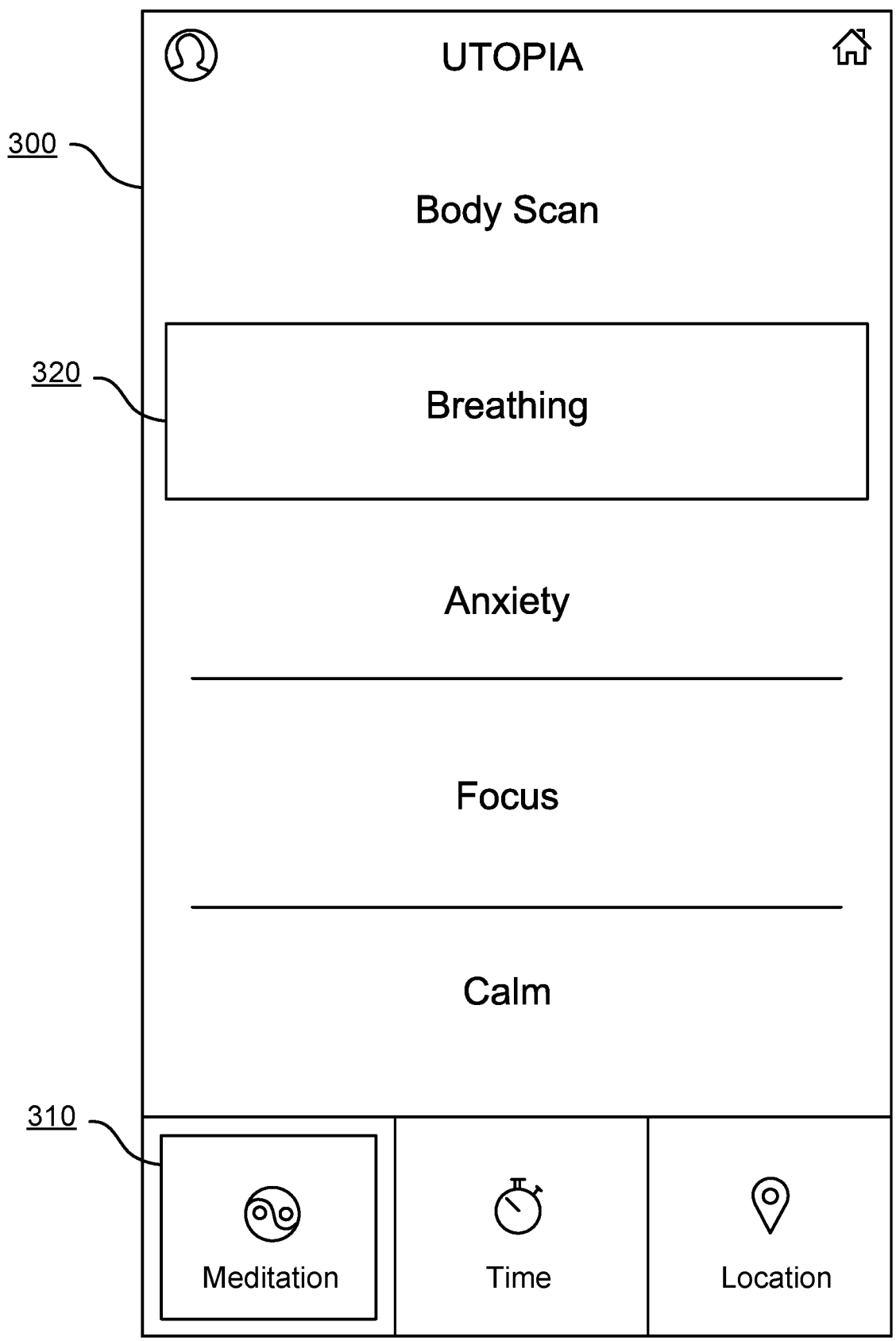
FIG. 3 is user interface illustrating meditation types of the VR guided meditation system according to one embodiment.

FIG. 3 is user interface 300 illustrating meditation types of the VR guided meditation system 100 according to one embodiment. The user interface 300 shown in FIG. 3, e.g., generated by the guided meditation module 215, includes a selection 310 to display types of meditation for a VR guided meditation exercise and selection 320 of a type of meditation. Types of meditations illustrated in the user interface 300 include "body scan," "breathing," "anxiety," "focus," and "calm." In other embodiments, the user interface 300 includes fewer, additional, and/or different types of meditations. In the example shown in FIG. 3, the selection 320 indicates that the user 115 wants a breathing type of meditation. The guided meditation module 215 receives the indication and provides a VR guided meditation exercise based on the indication. In an embodiment, the guided meditation module 215 stores the indication in the user account store 240 along with a user account associated with the user 115.

In one example, a VR guided meditation exercise corresponding to a breathing type of meditation focuses on breathing patterns of a user 115. For instance, the guided meditation module 215 generates visual and/or audio instructions of the VR guided meditation exercise notifying the user 115 to "inhale slowly over 4 seconds," "hold your breath for 7 seconds," and "exhale slowly over 8 seconds." In an embodiment, the guided meditation module 215 synchronizes the instructions with a visual element and/or an event in a VR environment generated by the VR engine 210. For example, the VR environment corresponds to a "garden falls" location (e.g., the garden falls location in FIG. 3), so the VR environment includes visual and/or audio signals of a waterfall. The guided meditation module 215 synchronizes the instructions with the visual and/or audio signals of the waterfall. In particular, the instruction "exhale slowly over 8 seconds" is synchronized with a visual signal of a large wave of water splashing in the waterfall and an audio signal corresponding to the splashing of the wave of water. As another example, the instruction may generally include asking the user to look at scenery (regardless of what it is) while the user is imagining walking through the scenery. The user 115 can more easily follow the instruction when assisted with cues from the visual and/or audio signals, e.g., because the imagery and/or sound of a waterfall often help users relax their minds and concentrate on their breathing patterns. Accordingly, synchronizing the instructions with the visual and/or audio signals provides an improved user experience to the user 115. In some embodiments, the visual and/or audio instructions correspond to an event and/or a visual element of the VR environment. For example, an audio instruction, "look at the bottom of the waterfall as you exhale," instructs the user to 115 to look at a particular object and/or location while completing the VR guided meditation exercise.

In another example, a VR guided meditation exercise corresponding to a body scan type of meditation focuses on parts of a body of a user 115. For instance, the guided meditation module 215 generates visual and/or audio instructions of the VR guided meditation exercise notifying the user 115 to "let your shoulders be soft," "if you stomach is tight, let it soften," and "notice the weight of your feet on the ground." In an embodiment, the guided meditation module 215 synchronizes the instructions with a visual element and/or an event in a VR environment generated by the VR engine 210. For example, the VR environment corresponds to a "paradise beach" location (e.g., the paradise beach location in FIG. 3), so the VR environment includes visual and/or audio signals of a beach and ocean waters. The guided meditation module 215 synchronizes the instructions with the visual and/or audio signals of the beach and ocean waters. In particular, the instruction "notice the weight of your feet on the ground" is synchronized with a visual signal of sand blowing beneath the user 115 and an audio signal corresponding to the sound of the sand blowing. The user 115 can more easily follow the instruction when assisted with cues from the visual and/or audio signals, e.g., because the imagery and/or sound of beach and ocean often help users relax their minds and concentrate on their breathing patterns. Accordingly, synchronizing the instructions with the visual and/or audio signals provides an improved user experience to the user 115.

FIG. 4 is user interface 400 illustrating meditation time durations of the VR guided meditation system 100 according to one embodiment. The user interface 400 shown in FIG. 4, e.g., generated by the guided meditation module 215, includes a selection 410 to display time durations of meditation for a VR guided meditation exercise and selection 420 of a time duration of meditation. Time durations of meditations illustrated in the user interface 400 include "2 minutes," "5 minutes," and "10 minutes." In other embodiments, the user interface 400 includes fewer, additional, and/or different time durations of meditations. In the example shown in FIG. 4, the selection 420 indicates that the user 115 wants a 2 minute time duration of meditation. The guided meditation module 215 receives the indication and provides a VR guided meditation exercise based on the indication. In an embodiment, the guided meditation module 215 stores the indication in the user account store 240 along with a user account associated with the user 115.

Figure 5:
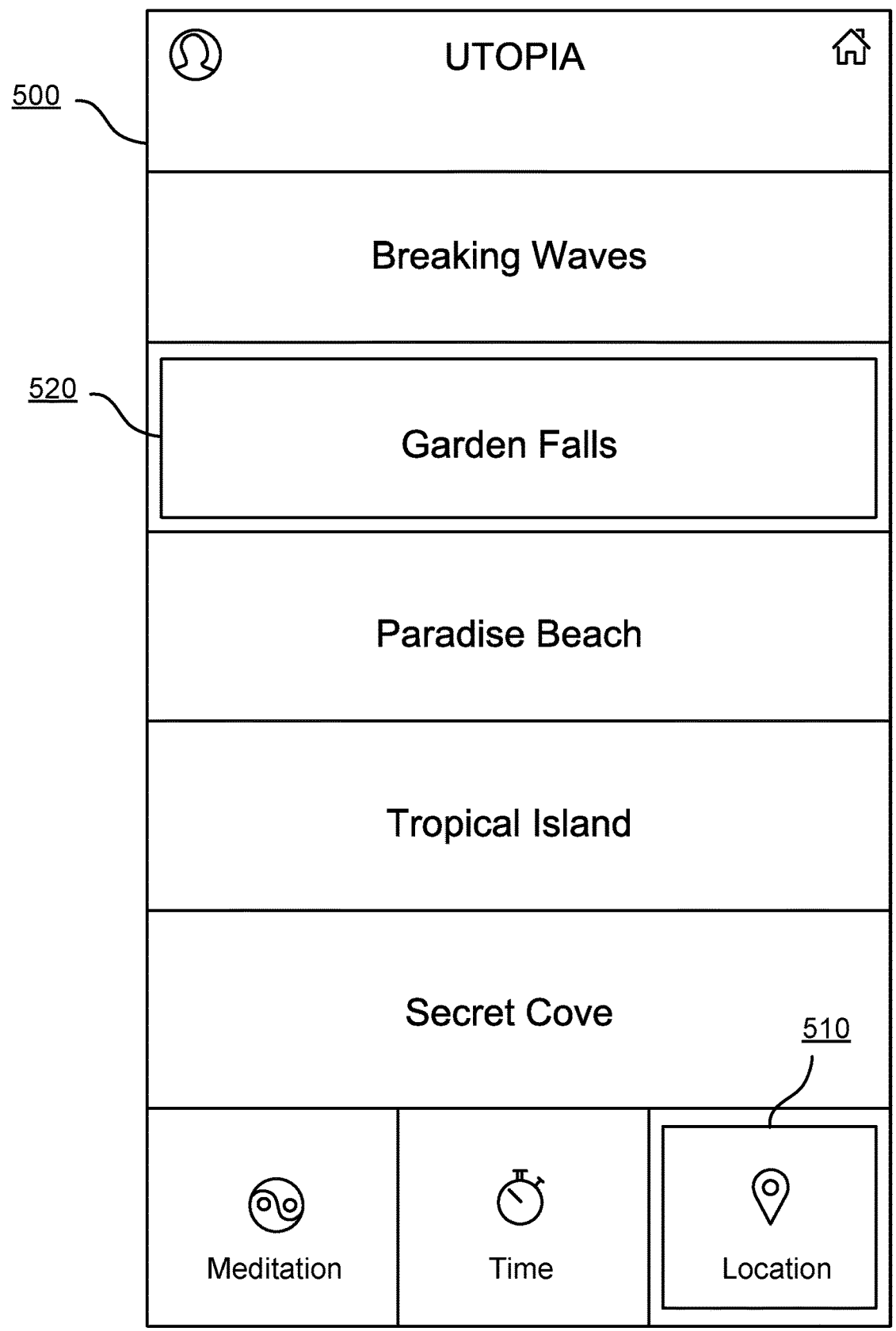
FIG. 5 is user interface illustrating meditation locations of the VR guided meditation system according to one embodiment.

FIG. 5 is user interface 500 illustrating meditation locations of the VR guided meditation system 100 according to one embodiment. The user interface 500 shown in FIG. 5, e.g., generated by the guided meditation module 215, includes a selection 510 to display locations of meditation for a VR guided meditation exercise and selection 520 of a location of meditation. Locations of meditations illustrated in the user interface 500 include "breaking waves," "garden falls," "paradise beach," "tropical island," and "secret cove." In other embodiments, the user interface 500 includes fewer, additional, and/or different locations of meditations. In the example shown in FIG. 5, the selection 520 indicates that the user 115 wants a "garden falls" location of meditation. The guided meditation module 215 receives the indication and provides a VR guided meditation exercise based on the indication. In an embodiment, the guided meditation module 215 stores the indication in the user account store 240 along with a user account associated with the user 115.

Meditation Based Feedback

Figure 6:
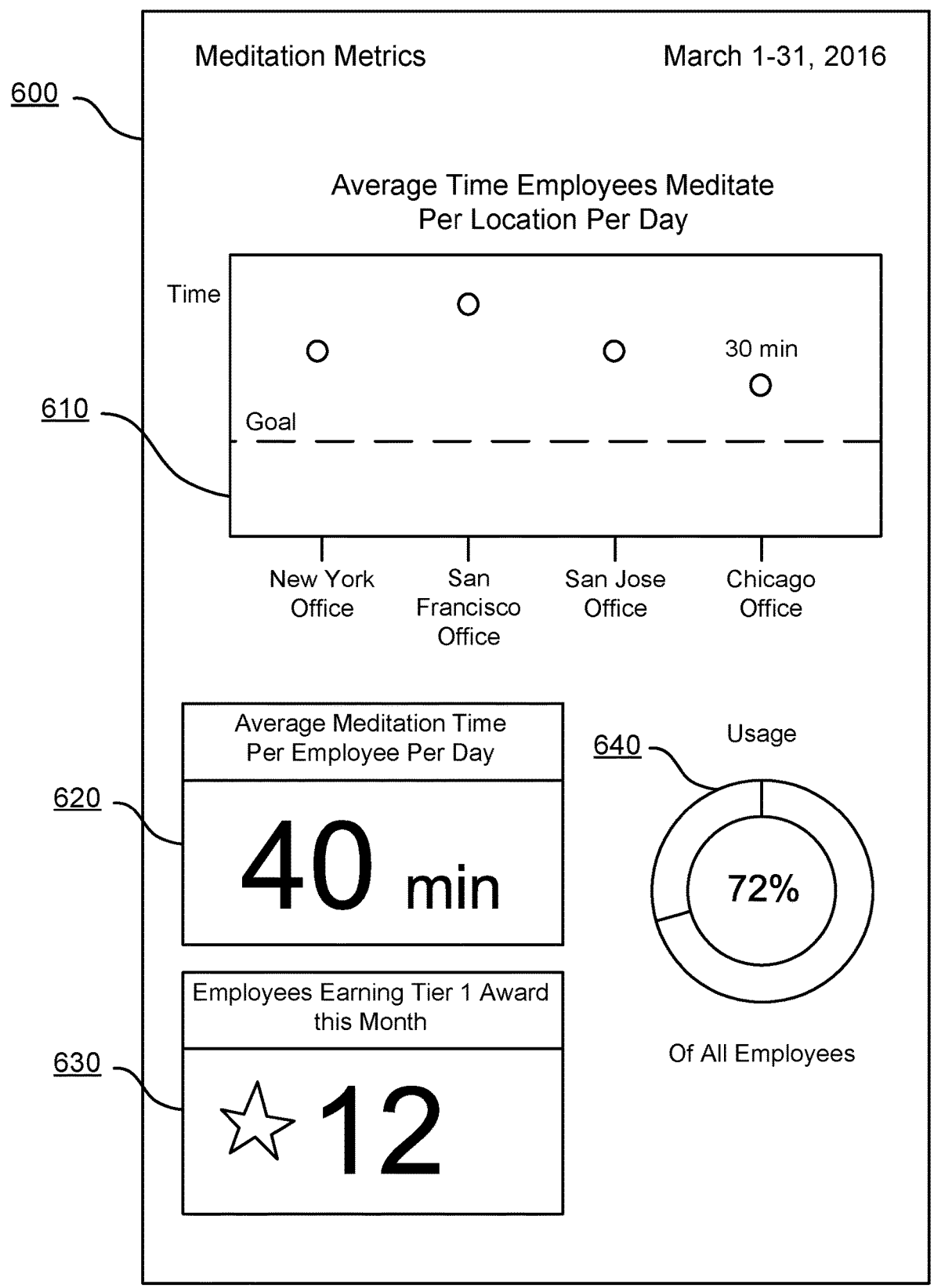
FIG. 6 is user interface illustrating meditation based feedback of the VR guided meditation system according to one embodiment.

FIG. 6 is user interface 600 illustrating meditation based feedback (e.g., "meditation metrics") of the VR guided meditation system 100 according to one embodiment. The user interface 600 is associated with an employer 125 and employees, i.e., user 115, of the employer 125 who complete VR guided meditation exercises. The user interface 600 shown in FIG. 6, e.g., generated by the report module 225, includes a chart 610 indicating the average time employees meditate per location (e.g., office location of the employer) per day, a display 620 of the average meditation time per employee per day, a display 630 of the number of employees earning tier 1 award this month, and a chart 640 indicating the usage percentage of the VR guided meditation system 100 among all employees. Other embodiments of the user interface 600 include additional, fewer, and/or different types of meditation based feedback from those shown in FIG. 6.

The chart 610 includes different office locations on the x-axis, i.e., New York Office, San Francisco Office, San Jose Office, and Chicago Office. The y-axis of the chart 610 represents the average time (e.g., in minutes) that employees at each office location meditates per day. For instance, employees at the Chicago office meditate on average for 30 minutes each day. The average time shown in FIG. 6 is based on VR guided meditation exercises completed in a current month, i.e., the month of "Mar. 1-31, 2016." The average time may also be based on information over a day, week, year, and/or any other time duration. The chart 610 also includes a dashed line indicating a goal for the average time that employees at each office location meditate per day, e.g., a goal of averaging 25 minutes per day. In an embodiment, the employer 125 manually selects the average time for the goal. In other embodiments, the VR guided meditation system 100 automatically sets the average time for the goal is based on meditation information about a population of users 115 of the VR guided meditation system 100. For example, the average time for the goal is based on the average time that the top 25% of users 115 in the population spend meditating. The population may include only employees of the employer 125 and/or other users 115 of the VR guided meditation system 100, e.g., employees from multiple employers 125 aggregated together.

The display 620 indicates that employees of the employer 125 meditate for an average of 40 minutes per day over a certain time period (e.g., over the current month, week, day, etc.). The display 630 indicates that 12 employees of the employer 125 have earned a tier 1 award in the current month (i.e., Mar. 1-31, 2016). The chart 640 indicates that 72% of all employees of the employer 125 use VR guided meditation system 100, e.g., 72% of all employees have completed at least one VR guided meditation exercise.

Process Flow

Figure 7:
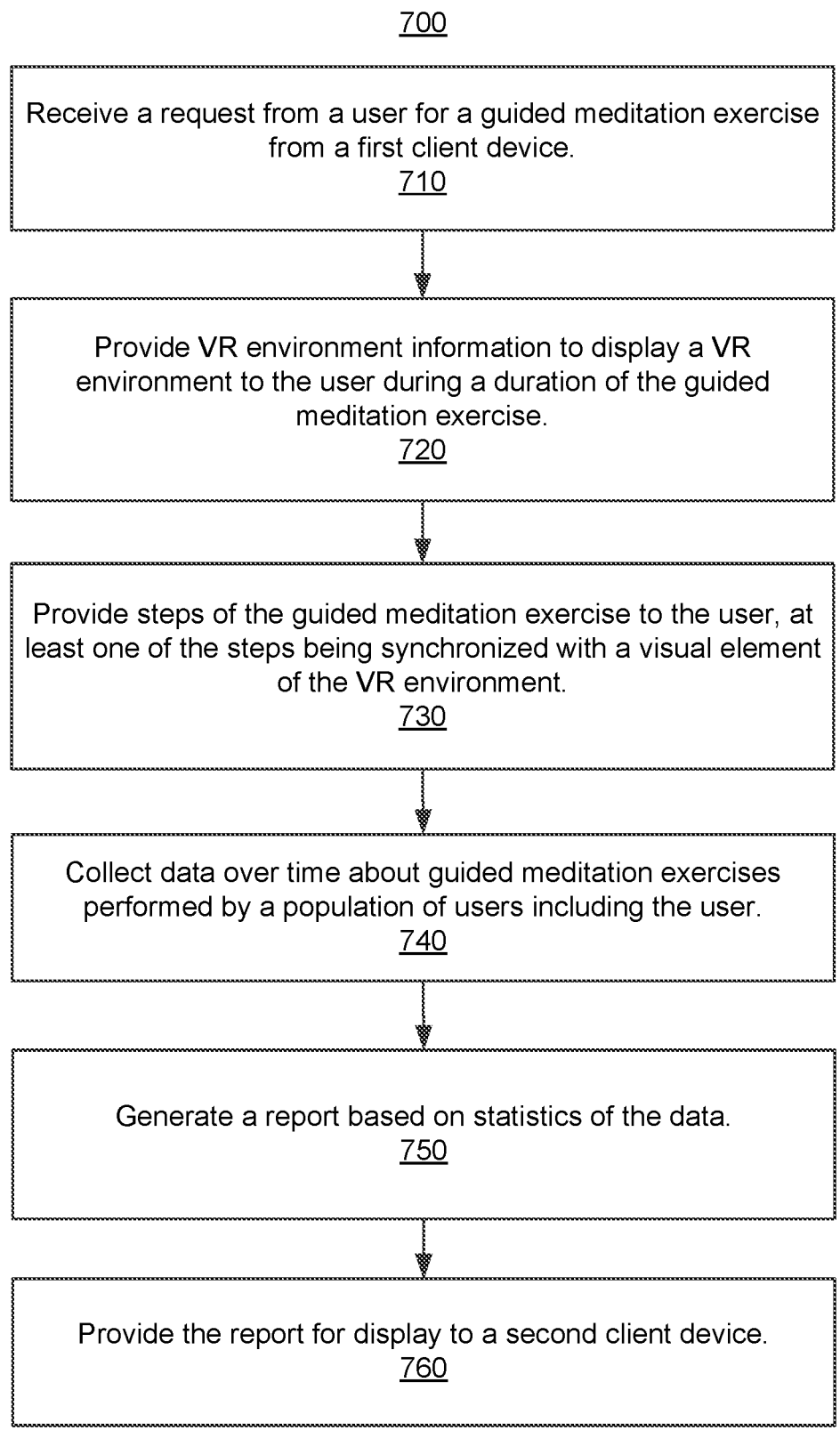
FIG. 7 is a flow chart illustrating a process for providing guided meditation according to one embodiment.

FIG. 7 is a flow chart illustrating a process 700 for providing guided meditation according to one embodiment. In some embodiments, the process 700 is used within the computing environment of FIG. 1. The process 700 may include different or additional steps than those described in conjunction with FIG. 7 in some embodiments, or perform steps in different orders than the order described in conjunction with FIG. 7.

In an example embodiment of the VR guided meditation system 100 using the process 700, the user interface module receives 710 user information from a client device 110 of a user 115. The user information may include a request from the user 115 for a guided meditation exercise, information indicating a type of VR environment for the guided meditation exercise, a duration of the guided meditation exercise, a type of guided meditation exercise, among other types of information. In response to the request from the user 115, the guided meditation module 215 provides 720 VR environment information for the guided meditation exercise to the client device 110. Based on the VR environment information, the client device 110 displays a VR environment (e.g., a VR environment corresponding to the "garden falls" location shown in FIG. 5) to the user 115 during the guided meditation exercise. The VR Engine 210 provides 730, with the VR environment, one or more steps of the guided meditation exercise to the client device 110. At least one of the one or more steps of the guided meditation exercise may be synchronized with a visual element of the VR environment. The user 115 can perceive the visual element while performing the guided meditation exercise, i.e., the user's eyes are open while performing the guided meditation exercise. For example, the visual element is a waterfall, a pebble on a beach, or a bird in the VR environment. In some embodiments, the visual element is an event occurring within the VR environment. For example, the event can be a splash of water in a waterfall, a bird flying over a beach, or a leaf falling from a tree.

Following in the same example embodiment, the report module 220 collects 740 data over a period of time about guided meditation exercises performed by a population of users on a multiple client devices. The population may include the user 115. Further, the population of users may be based on categories such as demographic information (e.g., age or gender of users), location information (e.g., geographical location of an office of users), and/or other types of information. The report module 220 generates 750 a report based at on statistics of the data collected about the guided meditation exercises performed by the population of users. For example, the report includes visual representations such as bar graphs, pie charts, line graphs, etc., of the statistics. The statistics may include, e.g., a mean or standard deviation of an amount of time that users 115 meditate using the VR guided meditation system 100 over a given time period (e.g., daily or weekly), a number of users 115 who achieved a particular goal and/or received a particular incentive, and the like. The VR guided meditation system 100 (e.g., the user interface module 200) provides 760 the report for display to a client device 120. The client device 120 may be used by an employer 125 of the user 115 to view and/or interact with the report and/or other reports, among other functions. For example, the employer 125 using the client device 120 may input information to set a goal for users performing the guided meditation exercises, send messages such as words of encouragement and status updates to the users, input information for incentives (e.g., which may correspond to a goal), retrieve information about users 115 of the VR guided meditation system 100, invite new users to use the VR guided meditation system 100 (e.g., by sending an email or text message invitation), and the like.

In an example use case with a smart phone client device 110, the user 115 positions the smart phone in his or her vicinity while completing a VR guided meditation exercise. The smart phone is positioned such that the user 115 can view a VR environment presented on the smart phone and listen to audio instructions of the VR guided meditation exercise played by the smart phone. In another example use case, a smart phone client device 110 is movably coupled to a VR head-mounted display (HMD) that needs to be used in conjunction with a smart phone, for example, Google® Cardboard and Samsung® Gear VR. In this use case, the user 115 wears the HMD and views the VR environment on a display of the smartphone positioned in front of the user's eyes. In yet another example use case, the client device 110 is a VR head-mounted display (HMD) that does not need to be used in conjunction with a smart phone, for example, Oculus® Rift. In this use case, the user 115 wears the HMD, views the VR environment on a display of the HMD, and listens to audio instructions of the VR guided meditation exercise played by audio speakers of the HMD.

ALTERNATIVE EMBODIMENTS

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a nontransitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a nontransitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

We claim:

1. A computer-implemented method for providing guided meditation to a population of users associated with a plurality of locations, comprising:

for each user of the population:

receiving, by a processor, user information from a first client device of the user, the user information including a request from the user for a guided meditation exercise, in response to the request from the user, providing, by the processor, virtual reality environment information for the guided meditation exercise to the first client device for the first client device to display a virtual reality environment to the user during a duration of the guided meditation exercise, providing, by the processor, with the virtual reality environment displayed on the first client device, one or more steps of the guided meditation exercise to the first client device, at least one of the one or more steps of the guided meditation exercise being synchronized with a visual element of the virtual reality environment that is perceptible to the user while performing the guided meditation exercise, and collecting, by the processor, data over a period of time about guided meditation exercises performed by the user on the first client device;

storing, by the processor, the collected data for the population of users;

generating, by the processor, reports for the population of users, each of the reports including a representation of statistics about the collected data for users associated with one of the plurality of locations;

providing, by the processor, the reports for display to a second client device of a coordinator of guided meditation exercises for users of the population;

for each location of the plurality of locations:

receiving, by the processor from the second client device, a respective goal of the guided meditation exercises, the respective goal generated based on the report for the location, the respective goal being specific to the location, and updating, by the processor, the virtual reality environment information for the guided meditation exercises of the users associated with the location based on the respective goal specific to the location; and providing, by the processor, the updated virtual reality environment information for the guided meditation exercises to the first client devices of the population of users.

2. The method of claim 1, wherein the user information comprises selections from the user regarding the virtual reality environment indicating a type of the virtual reality environment to be displayed to the user, the duration of the guided meditation exercise, and a type of the guided meditation exercise to be performed by the user.

3. The method of claim 1, wherein the coordinator is an employer who provides guided meditation exercises, and wherein the population of users are employees who are provided the guided meditation exercises to perform through a workplace wellness platform or as part of a health promotion program.

4. The method of claim 1, wherein the representation of the statistics of the report include at least a bar graph, a pie chart, or a line graph.

5. The method of claim 1, wherein providing, by the processor, with the virtual reality environment displayed on the first client device, the one or more steps of the guided meditation exercise to the first client device further comprises:
 providing, by the processor, one or more questions to the first client device for display to the user before the user starts the guided meditation exercise;
 receiving, by the processor from the client device, a first set of one or more answers to the one or more questions;
 providing, by the processor, the one or more questions to the first client device for display to the user after the user has completed the guided meditation exercise;
 receiving, by the processor from the first client device, a second set of one or more answers to the one or more questions; and
 storing, by the processor, the first set of one or more answers and the second set of one or more answers,
 wherein generating, by the processor, the report is further based on the first set of one or more answers and the second set of one or more answers.

6. The method of claim 5, wherein at least one answer of the first set of one or more answers indicates one of: strongly disagree, agree, neutral, disagree, and strongly disagree, and wherein at least one answer of the second set of one or more answers indicates one of: strongly disagree, agree, neutral, disagree, and strongly disagree.

7. The method of claim 1, wherein at least one of the one or more steps of the guided meditation exercise is associated with a body part or body function of the user and provides an instruction regarding the body part or body function for the user to follow during the guided meditation exercise.

8. The method of claim 1, wherein at least one of the one or more steps of the guided meditation exercise is associated with a breathing pattern of the user and provides an instruction regarding the breathing pattern for the user to follow during the guided meditation exercise.

9. A computer-implemented method for providing guided meditation to a population of users associated with a plurality of locations, comprising:
 for each user of the population:
  receiving, by a processor, user information from a first client device of the user, the user information including a request from the user for a guided meditation exercise,
  in response to the request from the user, providing, by the processor, virtual reality environment information for the guided meditation exercise to the first client device for the first client device to display a virtual reality environment to the user during a duration of the guided meditation exercise,
  providing, by the processor, with the virtual reality environment displayed on the first client device, one or more steps of the guided meditation exercise to the first client device, at least one of the one or more steps of the guided meditation exercise being synchronized with a visual element of the virtual reality environment that is perceptible to the user while performing the guided meditation exercise, and
  storing, by the processor, in response to the user performing the guided meditation exercise, information about the guided meditation exercise;
 for each location of the plurality of locations:
  receiving, by the processor from a second client device of a coordinator of guided meditation exercises for users of the population, a respective goal of the guided meditation exercise, the respective goal generated based on the stored information for users associated with the location, the respective goal being specific to the location, and
  determining, by the processor, incentive information for the users associated with the location based on the respective goal specific to the location, the incentive information indicating that the users have earned an incentive for at least some of the users achieving the respective goal by performing the guided meditation exercise; and
 providing, by the processor, the incentive information to the first client devices of the population of users.

10. The method of claim 9, wherein determining, by the processor, incentive information for users at a location is further based on information indicating that the users have completed a threshold number of guided meditation exercises.

11. A non-transitory computer-readable storage medium storing executable computer program instructions, the computer program instructions comprising code for:
 for each user of a population of users:
  receiving, by a processor, user information from a first client device of the user, the user information including a request from the user for a guided meditation exercise,
  in response to the request from the user, providing, by the processor, virtual reality environment information for the guided meditation exercise to the first client device for the first client device to display a virtual reality environment to the user during a duration of the guided meditation exercise,
  providing, by the processor, with the virtual reality environment displayed on the first client device, one or more steps of the guided meditation exercise to the first client device, at least one of the one or more steps of the guided meditation exercise being synchronized with a visual element of the virtual reality environment that is perceptible to the user while performing the guided meditation exercise, and
  collecting, by the processor, data over a period of time about guided meditation exercises performed by the user on the first client device;
 storing, by the processor, the collected data for the population of users;
 generating, by the processor, reports for the population of users, each of the reports including a representation of statistics about the collected data for users associated with one of the plurality of locations;

providing, by the processor, the reports for display to a second client device of a coordinator of guided meditation exercises for users of the population;

for each location of the plurality of locations:
  receiving, by the processor from the second client device, a respective goal of the guided meditation exercises, the respective goal generated based on the report for the location, the respective goal being specific to the location, and
  updating, by the processor, the virtual reality environment information for the guided meditation exercises of the users associated with the location based on the respective goal specific to the location; and providing, by the processor, the updated virtual reality environment information for the guided meditation exercises to the first client devices of the population of users.

12. The computer-readable storage medium of claim 11, wherein the user information comprises selections from the user regarding the virtual reality environment indicating a type of the virtual reality environment to be displayed to the user, the duration of the guided meditation exercise, and a type of the guided meditation exercise to be performed by the user.

13. The computer-readable storage medium of claim 11, wherein the coordinator is an employer who provides guided meditation exercises, and wherein the population of users are employees who are provided the guided meditation exercises to perform through a workplace wellness platform or as part of a health promotion program.

14. The computer-readable storage medium of claim 11, wherein the representation of the statistics of the report include at least a bar graph, a pie chart, or a line graph.

15. The computer-readable storage medium of claim 11, wherein providing, by the processor, with the virtual reality environment displayed on the first client device, the one or more steps of the guided meditation exercise to the first client device further comprises:
  providing, by the processor, one or more questions to the first client device for display to the user before the user starts the guided meditation exercise;
  receiving, by the processor from the client device, a first set of one or more answers to the one or more questions;
  providing, by the processor, the one or more questions to the first client device for display to the user after the user has completed the guided meditation exercise;
  receiving, by the processor from the first client device, a second set of one or more answers to the one or more questions; and
  storing, by the processor, the first set of one or more answers and the second set of one or more answers,
  wherein generating, by the processor, the report is further based on the first set of one or more answers and the second set of one or more answers.

16. The computer-readable storage medium of claim 15, wherein at least one answer of the first set of one or more answers indicates one of: strongly disagree, agree, neutral, disagree, and strongly disagree, and wherein at least one answer of the second set of one or more answers indicates one of: strongly disagree, agree, neutral, disagree, and strongly disagree.

17. The computer-readable storage medium of claim 11, wherein at least one of the one or more steps of the guided meditation exercise is associated with a body part or body function of the user and provides an instruction regarding the body part or body function for the user to follow during the guided meditation exercise.

18. The computer-readable storage medium of claim 11, wherein at least one of the one or more steps of the guided meditation exercise is associated with a breathing pattern of the user and provides an instruction regarding the breathing pattern for the user to follow during the guided meditation exercise.

19. The method of claim 1, further comprising receiving, by the processor, at least some of data about the user from a third party device that collects information about the user and is integrated with the first client device of the user.

20. The method of claim 1, wherein the virtual reality environment is provided for the users via a virtual reality head-mounted display worn by the users and programmed to provide the guided meditation exercises, wherein the virtual reality head-mounted display that is integrated with or separate from the first client device of each of the users.

* * * * *